United States Patent
Sauer et al.

(10) Patent No.: US 6,249,001 B1
(45) Date of Patent: Jun. 19, 2001

(54) INFRARED IMAGER USING ROOM TEMPERATURE CAPACITANCE SENSOR

(75) Inventors: Donald Jon Sauer, Allentown; Ramon Ubaldo Martinelli, Hightstown; Robert Amantea, Manalapan; Peter Alan Levine, Trenton, all of NJ (US)

(73) Assignee: Sarnoff Corporation, Princeton, NJ (US)

( * ) Notice: Subject to any disclaimer, the term of this patent is extended or adjusted under 35 U.S.C. 154(b) by 0 days.

(21) Appl. No.: 09/300,986

(22) Filed: Apr. 8, 1999

Related U.S. Application Data

(62) Division of application No. 08/818,554, filed on Mar. 14, 1997, now Pat. No. 5,965,886, which is a continuation of application No. 08/622,263, filed on Mar. 27, 1996, now Pat. No. 5,844,238.

(51) Int. Cl.[7] ............................. G01J 3/42; G01N 27/00
(52) U.S. Cl. .............................. 250/338.1; 250/336.1
(58) Field of Search ............................ 250/332, 338.1, 250/340, 336.1; 374/205

(56) References Cited

U.S. PATENT DOCUMENTS

| | | |
|---|---|---|
| 2,482,440 | 9/1949 | Rylsky . |
| 3,384,749 | 5/1968 | Golay . |
| 3,415,712 | 12/1968 | Barker, Jr. . |
| 3,657,644 | 4/1972 | Beam et al. . |
| 3,896,309 * | 7/1975 | Halsor et al. ............... 250/370 |
| 4,287,441 | 9/1981 | Smith . |
| 4,652,766 | 3/1987 | Wang et al. . |
| 4,659,928 | 4/1987 | Tew . |
| 4,660,090 | 4/1987 | Hynecek . |
| 4,675,739 | 6/1987 | Catchpole et al. . |
| 4,681,440 | 7/1987 | Burke et al. . |
| 4,683,580 | 7/1987 | Matsunaga . |
| 4,779,004 | 10/1988 | Tew et al. . |
| 4,786,831 | 11/1988 | Morse et al. . |
| 4,875,098 | 10/1989 | Yamamoto et al. . |
| 4,902,886 | 2/1990 | Smisko . |
| 4,943,491 | 7/1990 | Norton et al. . |
| 5,144,133 | 9/1992 | Dudley et al. . |
| 5,182,624 | 1/1993 | Tran et al. . |
| 5,290,102 | 3/1994 | Kaiser et al. . |
| 5,293,041 * | 3/1994 | Kruse ............................... 250/338.3 |
| 5,420,428 | 5/1995 | Bullington et al. . |
| 5,436,452 | 7/1995 | Kenny et al. . |
| 5,449,908 | 9/1995 | Wadsworth et al. . |
| 5,471,515 | 11/1995 | Fossum et al. . |
| 5,747,804 | 5/1998 | Williams et al. . |
| 5,929,440 | 7/1999 | Fisher . |
| 5,965,886 * | 10/1999 | Sauer et al. ......................... 250/332 |

FOREIGN PATENT DOCUMENTS

| | | |
|---|---|---|
| WO 95/02170 | 1/1995 | (WO) . |
| WO 95/02180 | 1/1995 | (WO) . |
| WO 96/08701 | 3/1996 | (WO) . |

OTHER PUBLICATIONS

Gimzewski et al, "Observation of a Chemical Reaction Using a Micromechanical Sensor", Chem. Phys. Lett. v. 217, No. 5,6 p. 589, Jan. 28, 1994.*

(List continued on next page.)

Primary Examiner—Georgia Epps
Assistant Examiner—Richard Hanig
(74) Attorney, Agent, or Firm—William J. Burke; Abhik A. Huq

(57) ABSTRACT

An infrared imager includes an array of capacitance sensors that operate at room temperature. Each infrared capacitance sensor includes a deflectable first plate which expands due to absorbed thermal radiation relative to a non-deflectable second plate. In one embodiment each infrared capacitance sensor is composed of a bi-material strip which changes the position of one plate of a sensing capacitor in response to temperature changes due to absorbed incident thermal radiation. The bi-material strip is composed of two materials with a large difference in thermal expansion coefficients.

7 Claims, 10 Drawing Sheets

OTHER PUBLICATIONS

Barnes et al., "Photothermal Spectroscopy with Femtojoule Sensitivity Using a Micromechanical Device"; Nature vol. 372 No. 3 p. 79, Nov. 1994.*

S. Horn and R. Buser, "Night Vision and Electronic–Sensors Directorate", SPIE, vol. 2020, Infrared Technology XIX, pp 304–321, Apr., 1993.

R.A. Wood, "Uncooled thermal imaging with monolithic silicon focal planes", SPIE, vol. 2020 Infrared Technology XIX, pp. 322–329, Apr., 1993.

C. Hanson, "Uncooled thermal imaging at Texas Instruments", SPIE vol. 2020 Infrared Technology XIX, pp. 330–339, Apr., 1993.

A. Jensen, "Limitations to Room Temperature IR Imaging Systems", SPIE, vol. 2020, Infrared Technology XIX, pp. 340–350, Apr., 1993.

P. W. Kruse, "Uncooled IR Focal Plane Arrays", SPIE, vol. 2552, pp 556–563, Jul., 1995.

W. Riethmüller and W. Benecke, "Thermally Excited Silicon Microactuators", IEEE Transactions on Electron Devices, vol. 35, No. 6, pp. 758–763, Jun., 1988.

W. Lang, K. Kühl and H. Sandmaier, "Absorbing layers for thermal infrared detectors", Sensors and Actuators, vol. A, No. 34, pp. 243–248, 1992.

Oden et al., "Optical and Infrared Detection Using Microcantilevers," Department of Physics, University of Tennessee, 10 pgs. (undated).

Barnes et al., Photochemical Spoectroscopy with Femtojoule Sensitivity using a Micromechanical Device Nature, vol. 372, No. 3, pp. 79–81, Nov. 1994.

* cited by examiner

INFRARED IMAGER USING ROOM TEMPERATURE CAPACITANCE SENSOR

This application is a division of Ser. No. 08/818,554 filed Mar. 14, 1997, U.S. Pat. No. 5,965,886, which is a continuation of Ser. No. 08/662,263 filed Mar. 27, 1996, U.S. Pat. No. 5,844,238.

FIELD OF THE INVENTION

This invention relates to room temperature capacitance sensor, and more particularly to a low-cost manufacturable infrared imager that operates at room temperature and has substantially improved performance approaching the theoretical background limited performance limit.

BACKGROUND OF THE INVENTION

Instruments for the measurement of infrared (IR) radiation are becoming increasingly important for a variety of commercial and non-commercial applications. Research into the development of uncooled sensors with response throughout the infrared spectrum has been particularly important due to the limitation on the operation of cooling systems. Uncooled infrared sensors would have important applications for space-based remote-sensing of thermal sources, night vision, target identification, thermal mapping, event detection, motion detection, and others. The limitations of the performance of the existing uncooled sensors often are the primary constraints to the performance of infrared imaging systems for many applications. As a result, there has been considerable investment in the development of uncooled infrared sensors.

A broad assortment of infrared detectors has been developed over the last 40 years. In most cases, they may be classified as either quantum or thermal detectors, depending upon whether the incoming radiation is converted to excitations which are collected, or is converted to heat and detected through changes in temperature. In general, a quantum detector which operates at detector temperatures Td is usually superior to a thermal detector at the same temperatures for infrared frequencies in which $hv >> k_B T_d$, where h is Plaiick's constant and $k_B$ is Boltzmann's constant. However, for infrared frequencies in which $hv << k_B T_d$. thermal detectors represent the only functional technology. The operation of quantum detectors is limited by the availability of efficient photon conversion mechanisms, while the operation of thermal detectors is limited by the availability of sensitive thermometers. Only thermal infrared sensors operate in the mid-to-far infrared range ($\lambda > 10$ $\mu$m) at room temperature.

The pneumatic infrared detector, which was originally developed by Golay, is classified as a thermal detector. Golay's detector consists of a small cavity filled with gas at room temperature. The cavity is separated from the surroundings by a window and a thin, flexible membrane. The membrane is coated on one side with a thin metallic film, which has significant absorption throughout the infrared spectrum whenever the sheet resistance of the film is approximately half of the impedance of free space. The trapped gas in the Golay cell is heated by contact with the membrane and expanded thermally, which forces the membrane to deflect outward. This deflection is usually detected with optical or capacitive displacement transducers. At present, these detectors are bulky, fragile, difficult to fabricate, and expensive. Nevertheless, they have been widely used, primarily because of their improvement in sensitivity over all other room-temperature detectors in the mid-to-far infrared range. Attempts to miniaturize the Golay cell for incorporation into focal plane arrays have been unsuccessful because of scaling laws which relate the sensitivity of conventional displacement transducers and their active area. The need for focal-plane arrays of uncooled detectors stimulated the development of pyroelectric detector arrays, the best of which are 5–10 times less sensitive than the Golay cell.

Current state-of-the-art uncooled IR focal plane arrays use many different thermal detection mechanisms such a bolometric (sensor resistance is modulated by temperature), pyroelectric (dielectric constant is modulated by temperature), and thermoelectric effects. As discussed above, thermo-mechanical effects have been explored using modifications of the Golay cell. The performance of IR imagers based on these technologies is limited compared with imagers based on direct photon conversion, such as PtSi detectors operated 77 K, and also is considerably worse than the theoretical background limited performance. In all approaches, the fundamental limits to the performance are controlled by the ability to thermally isolate the detector from its surroundings, the detector sensitivity to a change in temperature, and the introduction of extraneous noise sources. One of the reasons for degraded performance is the parasitic thermal resistance paths inherent in the supporting structures of the sensing elements. Another reason is the electronic noise present in the readout scanning circuitry.

With the above considerations in mind, the present invention is based on the development of an IR capacitance structure that deflects the position of a plate in response to temperature changes.

SUMMARY OF THE INVENTON

The present invention provides a high-performance infrared imager that operates at room temperature. More specifically, this invention uses an infrared (IR) capacitance structure to sense changes in temperature. Thermal energy deforms the structure of the present invention resulting in a deflection that determines a capacitance which is then sensed.

The present invention provides an infrared capacitance sensor composed of a bi-material strip which changes the position of one plate of a sensing capacitor in response to temperature changes due to absorbed incident thermal radiation. The physical structure of this capacitance sensor provides high thermal radiation resistance and high thermal sensitivity by utilizing a bi-material strip composed of two materials with a large difference in thermal expansion coefficients (e.g., $Si_3N_4$ and Al) mechanically supported by a long strip of material with high thermal resistance (e.g., $Si_3N_4$).

Additional embodiments within the scope of this invention are also possible. These embodiments are extensions of the basic IR capacitance structure and include (1) a bridge structure with a bi-material element for increased structural stability, (2) a bridge structure without a bi-material element, relying only on the thermal expansion and the "beam buckling concept" in which the two ends of the structure are pinned for increased process simplicity, and (3) variations where the support arms may be parallel or co-linear with the bi-material element.

Another aspect of this invention is the design and operation of a readout multiplexer for a focal plane imager made up of an array of these capacitance sensors.

Another aspect of this invention is the use of a correlated double sampling (CDS) circuit to reduce the 1/f noise and dc offset of the pixel amplifiers.

Another aspect of this invention is the use of 2x oversampling for both the reference and signal samples in the CDS readout circuit so that the mechanical resonant frequency of the capacitance sensor is at the Nyquist frequency of the samples.

Another aspect of this invention is that the readout method does not remove the signal which is stored as a change in capacitance.

The foregoing and other aspects of the present invention will become apparent from the following detailed description of the invention when considered in conjunction with the accompanying drawings.

BRIEF DESCRIPTION OF THE FIGURES

FIG. 3(*b*) is a top view of a 2-dimensional array of pixels.

FIGS. 5(*b*)–5(*m*) illustrate the processing steps for the formation of the pixel of FIG. 2.

DETAILED DESCRIPTION OF THE EXEMPLARY EMBODIMENTS

The present invention relates to a room temperature infrared imaging sensor which can reach a performance level, known as NEΔT, in the range of 1 degree milliKelvin (mK), which approaches the theoretical Limit of 0.36 mK. This invention, which is 100% compatible with silicon IC foundry processing, utilizes a novel combination of surface micromachining and conventional integrated circuit manufacturing techniques to produce a bi-material thermally sensitive element that controls the position of a capacitive plate coupled to the input of a low noise MIOS amplifier. This combination is able to produce a room temperature imager with sensitivity and imagery comparable to today's best cooled imagers at a cost comparable to visible imagers used in camcorders. This invention achieves the high sensitivity, the low weight and the low cost necessary for equipment such as helmet mounted IR viewers and IR rifle sights.

Table 1 shows a device characteristic comparison of the current invention versus conventional pyroelectric and bolometric devices.

TABLE 1

Comparison Summary

| Type | Sensitivity (V/K) | Isolation (K/W) | Responsivity (V/W) | NEΔT (mK) |
|---|---|---|---|---|
| Pyroelectric | 0.425 | $5 \times 10^5$ | $8.5 \times 10^4$ | 47 |
| Bolometric | 0.0056 | $1.25 \times 10^7$ | $7 \times 10^4$ | 40 |
| Bi-material | 1.08 | $1 \times 10^7$ | $1 \times 10^7$ | 2.6 |

The pixel design of the present invention has the following benefits: 1) an order of magnitude improvement in NEΔT due to extremely high sensitivity and low noise, 2) low cost due to 100% silicon IC compatibility, 3) high image quality at increased yield due to the ability to do pixel-by-pixel offset and sensitivity corrections on the imager, 4) no cryogenic cooler and no high vacuum processing are needed, and 5) applicability to commercial applications such as law enforcement and transportation safety.

Infrared Capacitance Sensor

Figure 1:
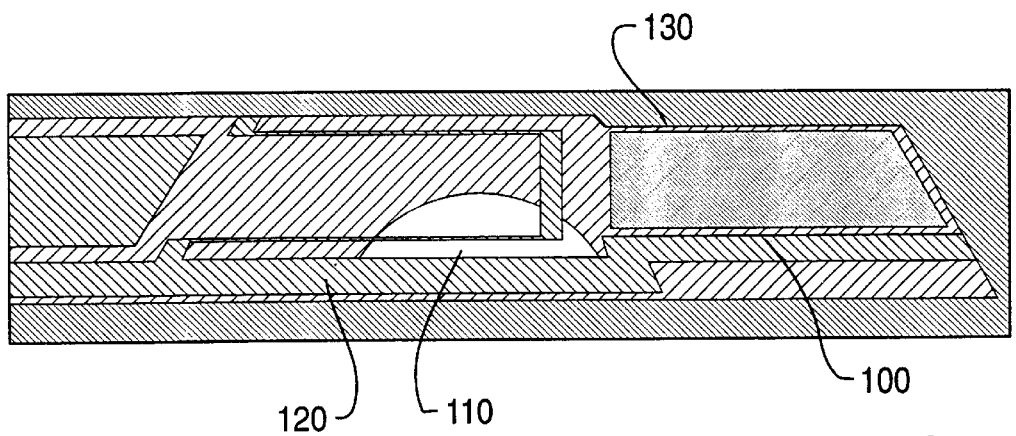
FIG. 1 illustrates a physical structure of an exemplary bi-material capacitance sensor in accordance with the present invention.

A physical structure of an exemplary bi-material capacitance sensor in accordance with the present invention is shown in FIG. 1. The capacitor plate 100 is mechanically supported in free-space (vacuum) by a bi-material strip 110 connected to a thermal isolation strip 120 which is anchored to the substrate on one end. The length/area ratio of the thermal isolation strip 120 is large to maximize the thermal resistance of this support. The bi-material strip 110 is composed of a bottom metal layer (e.g., aluminum) and a top layer (e.g., silicon nitride) which has a much lower thermal coefficient of expansion than the bottom layer. The top plate 100 of the capacitor is covered by a thermal radiation absorbing material 130 which causes temperature changes of the plate 100 in response to incident IR radiation. The heat absorbed in the plate 100 is conducted to the bi-material strip 110 by the bottom metal layer which has a relatively high thermal conductivity. The bi-material strip 110 and the capacitor plate 100 are linearly placed in order to maximize the displacement sensitivity.

Figure 2:
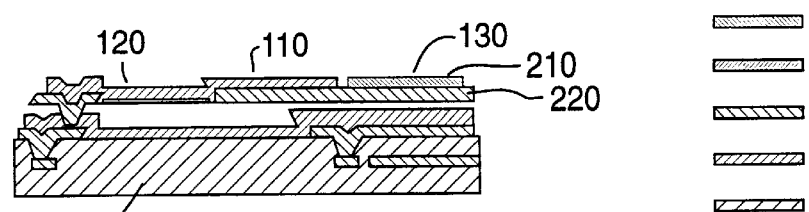
FIG. 2 illustrates a cross-section of a pixel showing the various elements that FIG. 1 comprises.
Figure 3A:
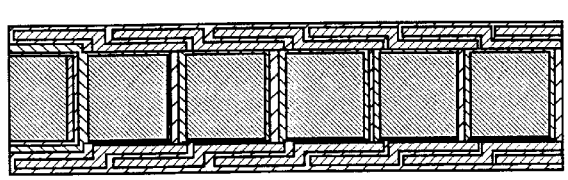
FIG. 3(*a*) is a top view of a linear array of pixels.
Figure 3B:
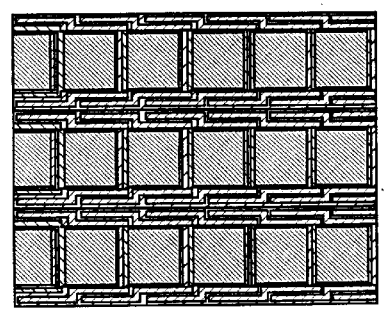

FIGS. 2, 3(*a*) and 3(*b*) show the essential features of a single pixel in a cross-section and multiple pixels in top view pictorial representations, respectively. In practice, the actual structure, positioning of the elements, and electronic addressing may vary considerably.

The sensor part of the pixel comprises three elements: the absorbing area 130 formed from a photon absorbing material 210 which overlays an electrically conductive plate 220, the area 130 converts IR radiation into heat; the bi-material element 110 that converts heat into mechanical movement (as in a home thermostat); and the thermally isolating support element 120 to prevent heat from being shunted down to the substrate 200. The electrically conductive plate may, for example, be aluminum, polysilicon or indium-tin oxide.

As described above, the bi-material element 110 is composed of two layers that differ greatly in their thermal linear expansion coefficient (described in Riethmuller, W. and Benecke, W., "Thermally Excited Silicon Microactuators", IEEE Trans. Electr. Dev. v35, n6, p758, June 1988, and which is hereby incorporated by reference for its teachings on thermal linear expansion coefficients). Since the two layers are bonded to one another, strain is built up and the structure bends, thereby moving the top plate of the capacitor with a sensitivity of $\alpha=(1/C)(\Delta C/\Delta T)\approx 40\%/°$ C. This is approximately 20 times greater than the sensitivity of vanadium oxide (having a sensitivity of approximately 2%/° C.) which is currently used in the most sensitive bolometers.

Figure 4:
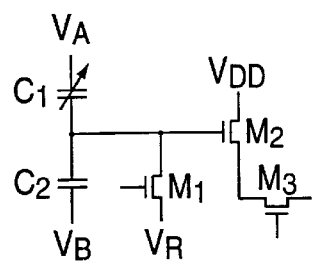
FIG. 4 is a schematic circuit diagram which is useful to describe pixel addressing.

The simplified circuit shown in FIG. 4 illustrates three applied signals, $V_A$, $V_B$ and $V_R$ and three transistors: the reset transistor $M_1$, the source follower amplifier $M_2$, and the row select transistor $M_3$. There are additional transistors (not shown) associated with $V_A$ and $V_B$ for controlling the submicrosecond sense pulses of opposite polarity applied to $C_1$ and $C_2$. If $C_2 V_B = -C_1 V_A$ then the nominal signal applied to the amplifier transistor is zero. Thus, the relative amplitudes of $V_B$ and $V_A$ can be used to adjust the offset at each pixel. Furthermore, $V_A$ can be used to adjust the gain at each pixel. Gain and offset correction at each pixel are desirable for optimizing image quality and increasing yield.

The manufacturing techniques used to manufacture the bi-material detectors include surface micro-machining steps as well as silicon IC processing which is compatible with, and transferable to standard silicon foundries.

Figure 5A:
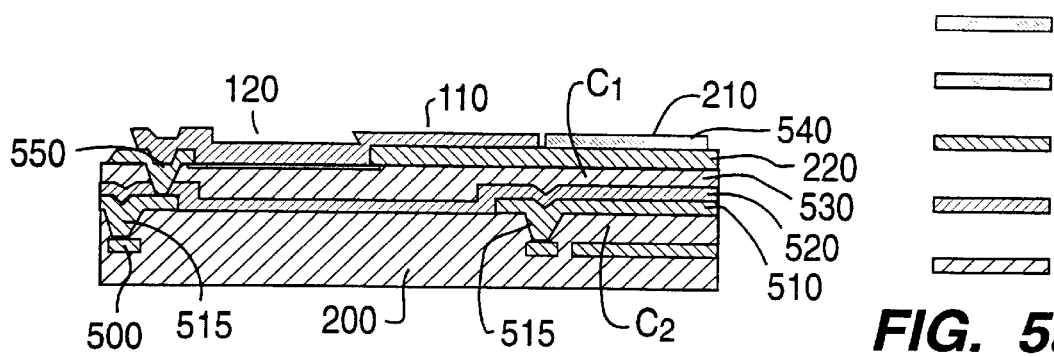
FIG. 5(*a*) illustrates a stylized cross-section of the pixel of FIG. 2.

FIG. 5(a) illustrates a stylized cross-section of a single pixel element with the uppermost layers of the IC at the bottom of the drawing. FIGS. 5(b)–5(m) illustrate the processing steps for the formation of the single pixel element. Note that the pixel element in FIGS. 5(a)–5(m) is a single, cantilever type pixel element. The IR pixel elements are surface micromachined above the surface of a single level metal CMOS IC.

Figure 5B:
Figure 5H:
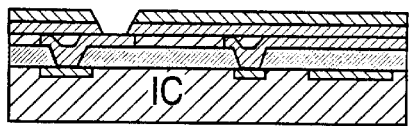
Figure 5C:
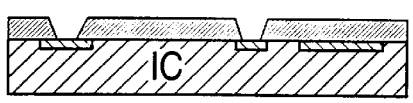

The fabrication of a pixel begins in FIG. 5(b) with the planarization of a metal-1 layer of an IC. The preferred planarization material 580 is a flowable oxide (FOX), approximately 800 nm thick. FIG. 5(c) shows an etch step used to define the via that will interconnect the pixel cantilever beam and the bottom plate of the sense capacitor $C_1$ 540.

Figure 5I:
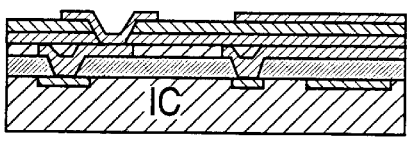
Figure 5D:
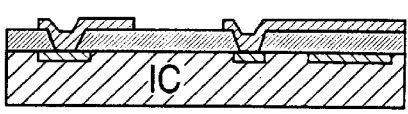

The fabrication of the surface pixel continues in FIG. 5(d) with the deposition and patterning of a metal-2 layer, for example, aluminum. The metal-2 layer is patterned to form a capacitor plate 510 and vias 515. It is desirable for the metal-2 layer to be 800 nm to 1000 nm thick with a 20 nm to 50 nm Ti layer (not shown) to suppress the formation of hillocks. In FIG. 5(e), a second planarization material 582 with a plasma etch-back is deposited to provide a uniformly planar surface for the top level capacitor definition.

Figure 5J:
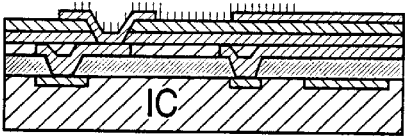
Figure 5E:
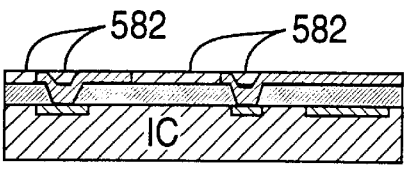
Figure 5K:
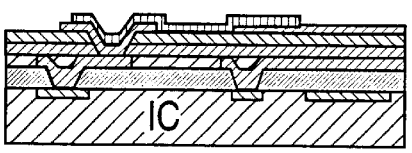
Figure 5F:

A dielectric overcoat layer 520 of silicon nitride or silicon carbide approximately 500 nm thick is then deposited in FIG. 5(f) and patterned to act as a "stop" layer to prevent electrical contact between the cantilevered capacitor plate 220, formed in metal-3 (e.g., aluminum), and the underlying plate 510 formed in metal-2.

It is desirable that the metal-1, metal-2 and metal-3 layers be electrically conductive. It should be noted that these layers can be aluminum, polysilicon or indium-tin oxide.

Figure 5L:
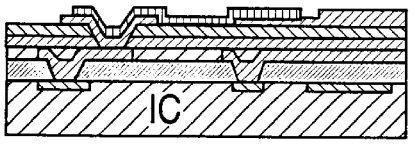
Figure 5G:

Fabrication continues in FIG. 5(g) with the deposition and patterning of a release layer 530 for the micromachined pixel element. The release layer 530 is typically an oxide layer between 200 and 500 nm thick, depending on the desired trade-off between thermal sensitivity and mechanical ruggedness. The release layer 530 can also be composed of polysilicon. The release layer 530 functions as both a spacer layer for the capacitor structure and the sacrificial material that will be etched completely away at the end of processing. Therefore, the properties of the release layer 530 should be chosen to be compatible with the other pixel structural layers.

It should be noted that the overcoat layer 520 and the release layer 530 thicknesses determine the gap of the sense capacitor $C_1$ 540 and therefore the thermal sensitivity. In FIG. 5(h), the overcoat layer 520 and the release layer 530 are etched to form the anchor structure for the pixel cantilever beam. This is a key process procedure since this anchor structure desirably has not only the correct wall profile, but also open a sufficiently large and clear opening to the metal-2 level below.

Fabrication continues in FIG. 5(i) with the deposition and patterning of the first bi-material component. This metal-3 layer is preferably 300 nm of aluminum and forms part of the bi-material structure 110, the top plate 220 of the sense capacitor 540, and the thermal conduction layer from the absorption area to the bi-material element.

The next layer to be deposited and patterned is the second component 560 of the bi-material structure, as shown in FIG. 5(j). This layer can be silicon carbide or silicon nitride, approximately 300 nm, and acts as the thermal isolation element between the pixel and the substrate.

FIG. 5(k) illustrates the deposition and patterning of a very thin interconnect metal layer 570, 20 nm to 40 nm thick, which makes an electrical connection between the via/anchor structure and the top plate of the sense capacitor 540. Platinum, titanium, titanium nitride or indium tin oxide are desirable materials for this step. This layer is desirably thin to provide only low levels of thermal conductivity.

Note that the two layers of the bi-material structure may be reversed with the deposition of the interconnection metal 570 placed between the nitride or carbide layer and the aluminum layer. However, this processing is more difficult.

The next step, shown in FIG. 5(l), is the deposition and patterning of the IR absorption layer 210 at the end of the cantilever beam assembly. This material can be evaporated black platinum, carbon black, black aluminum or other materials that have superior absorption properties. This layer may be patterned using conventional lift-off techniques. The layer thickness is determined by the extent to which the material "loads" the end of the pixel element.

Figure 5M:
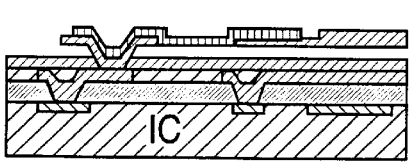

The final step, illustrated in FIG. 5(m), is the wet chemical etching of the release layer 530 to free the pixel element. A conventional etchant is used to remove the release layer 530. It is desirable to use an etchant that will not significantly remove any of the layers contacting the release layer 530. The element is then ready for bonding in a suitable package and testing.

In operation, thermal energy deforms the structure, thereby resulting in a deflection of the cantilever beam causing a change in the capacitance of the sense capacitor. As the deflection increases, the space between the plates of sense capacitor $C_1$ 540 increases, thereby decreasing the capacitance of the sense capacitor 540. The reversal of this thermal interaction, or vibration or electrostatic interaction between the plates 220 and 510 of the sense capacitor 540 may cause the top plate 220 of the sense capacitor 540 to crash into the overcoat layer 520 covering the lower plate 510 of the sense capacitor 540. This problem is mitigated by the addition of dimples to the structure.

Dimples are added to the structure by etching wells approximately one-third through the release layer 530 after the release layer 530 is deposited and patterned in FIG. 5(g). Then, when the first bi-material component is deposited in FIG. 5(i), the first bi-material component fills these wells, resulting in dimples on the side of the bi-material structure 110 contacting the release layer 530.

The vertical displacement of the center of the capacitor plate due to the bi-material affect can be shown to vary approximately as $dx/dt=0.72(\alpha_{Al}-\alpha_{siN})L^2/t$, where L is the length of the element, t is the thickness of each material, and $\alpha_x$ is the linear thermal expansion coefficient for material x. For t=0.2 $\mu$m and L=50 $\mu$m, $dx/dT=0.18$ $\mu$m/° C. For a 0.4 $\mu$m gap between metal-3 and the overlay and for a 0.4 $\mu$m overlay composed of $Si_3N_4$, the effective capacitor gap between metal-3 and metal-2 is 0.5 $\mu$m. Thus, the thermal sensitivity of the detection mechanism is $\alpha=(\Delta x/x\Delta T)(\Delta C/C\Delta T)=36\%/°$ C. The process and material design rules are compatible with current silicon foundries at 1 $\mu$m, which is three generations behind the state of the art. The use of these relaxed design rules results in low cost and high yield manufacturing. Analysis of the sense circuit of FIG. 8 (described in detail below) shows that the voltage response of the amplifier to a temperature change with $V_A=10$ V is $dV/dT=(\alpha/3)V_A \approx 1.2$ V/° C., where a is the thermal sensitivity. Alternative approaches such as vanadium oxide have a voltage response that is several orders of magnitude less than this.

Figure 6:
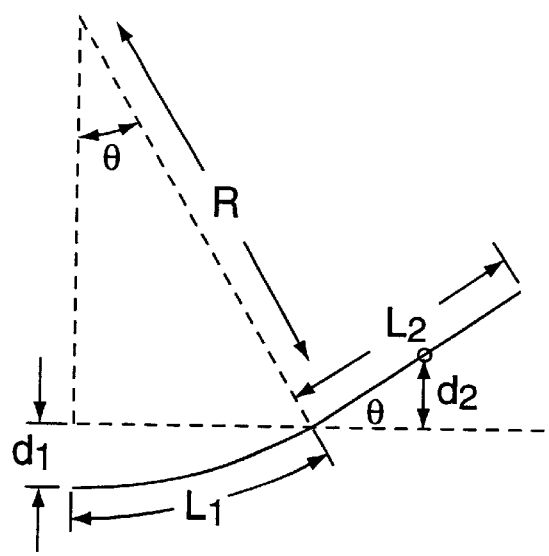
FIG. 6 is a geometric diagram of the exemplary device of FIG. 1.

A geometric representation of the structure of FIG. 1 is shown in FIG. 6 and is used for calculating the thermally induced deflection of the capacitor plate 100. The total displacement of the capacitor plate 100 is calculated as follows. For this analysis assume that the capacitor plate 100 remains planar and all of the bending occurs in the bi-material strip 110 connected to one end of the plate 100. This would occur if the absorber is very thin or if it has approximately the same thermal expansion coefficient as the aluminum layer that forms the upper plate of the sense capacitor $C_1$. The total displacement is taken from the center (average) distance of the capacitor plate 100 to a reference x-axis. This displacement d equals $d_1+d_2$ where $d_1$ is the displacement at the end of the bi-material strip 110 (given by equations (1) and (2)) and $d_2$ is the additional displacement at the center of the capacitor plate 100 (given by equation (3)). From FIG. 6:

$$d_1=R(1-\cos\theta) \tag{1}$$

where θ is the angle of deflection above the horizontal, in radians;

for θ<<1, $\cos\theta=1-\theta^2/2$ and $\sin\theta=\theta$, $$d_1=R\theta^2/2=(\text{where }\theta=L_1/R)L_1/2R \tag{2}$$

$$d_2=(L_2/2)\sin\theta=(L_1L_2)/(2R) \tag{3}$$

From an analysis of a bi-material strip (described in Shanley, F. R., "Strength of Materials", McGraw-Hill. 1957, p. 321, and which is hereby incorporated by reference for its teachings on bi-material strip analysis), equation (4) is obtained:

$$1/R=K\Delta T(\alpha_2-\alpha_1)/t, \tag{4}$$

where:
K is a correction factor due to the different Young's moduli of the two materials;
ΔT is the temperature differential:
$\alpha_2-\alpha_1$ is the difference in thermal expansion coefficients of the two materials; and
$t=t_1=t_2$ is the thickness of each layer.

Substituting (4) in (2) results in equation (5):

$$d_1=L_1^2K\Delta T(\alpha_2-\alpha_1)/2t \tag{5}$$

For the case where $L_1=L_2$, the total displacement is given by equation (6):

$$d=d_1+d_2=L_1^2K\Delta T(\alpha_2-\alpha_1)/t \tag{6}$$

As a practical example, d is calculated for the following conditions: the bi-material strip is aluminum/silicon nitride, $\alpha(Al)=23\times10^{-6}$, $\alpha(Si_3N_4)=2.8\times10^{-6}$, $L_1=L_2=50$ $\mu$m, t=0.5 $\mu$m, and K=0.72. Thus, d=0.073 $\mu$m/ΔT.

Figure 7:
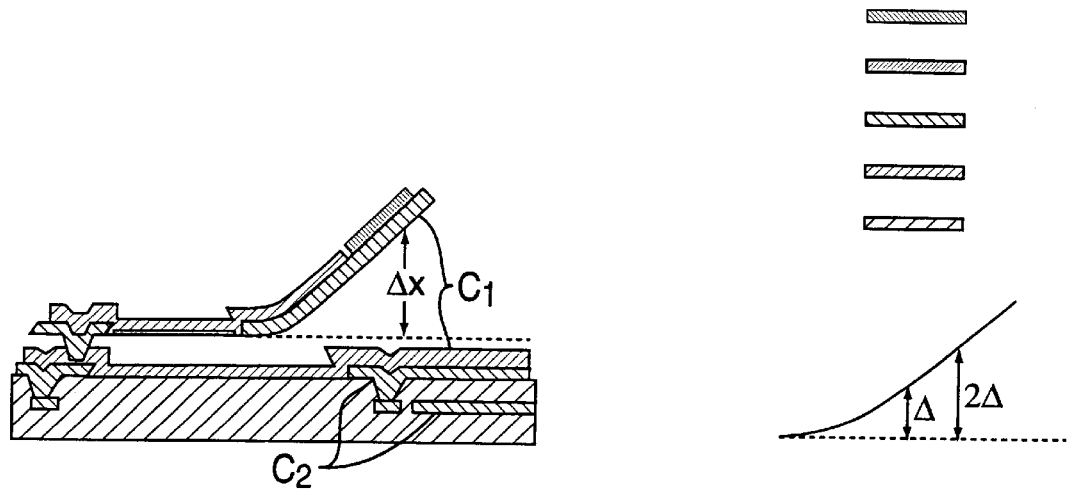
FIG. 7 illustrates a cross-section of an excited pixel showing the displacement of the capacitor.

FIG. 7 shows a cross-section pictorial representation of a single cantilever type pixel that is at a slightly elevated temperature relative to its nominal value. The bi-material effect (described in Shanley and which is hereby incorporated by reference for its teachings on bi-material effects) predicts the displacement at the end of the element due to a unit change in temperature to be $K\Delta\alpha L_b^2/2t_b$. For the cantilevered sensor, there is an additional displacement of the center of the absorber that doubles the sensitivity, e.g., $\Delta\alpha/\Delta T=K\Delta\alpha L_b^2/t_b$. Table 2, which contains design parameters, summarizes the high performance and low cost dimensions of the structure.

TABLE 2

Pixel Design Parameters

| Symbol | Definition | High Performance | Low Cost | Units |
|---|---|---|---|---|
| A | Pixel area | 2500 | 2500 | $\mu m^2$ |
| L | Pixel length | 50 | 50 | $\mu$m |
| $t_b$ | Bi-material layer thickness | 0.2 | 0.4 | $\mu$m |
| $t_r$ | Release layer thickness | 0.5 | 0.5 | $\mu$m |
| $t_c$ | Cap layer thickness | 0.3 | 0.5 | $\mu$m |
| s | Spacer | 1 | 3 | $\mu$m |
| $w_s$ | Support width | 2 | 4 | $\mu$m |
| $t_{vu}$ | Absorber-via connect thickness | 250 | 250 | Å |
| $V_A$ | Sensing voltage | 10 | 10 | Volt |

Figure 8:
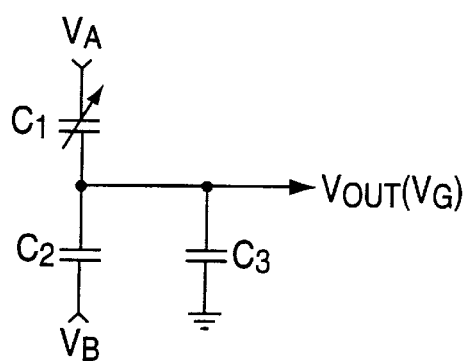
FIG. 8 is a schematic diagram of an exemplary front-end capacitance network in accordance with the present invention.

The voltage response of the pixel can be analyzed through the use of the equivalent circuit shown in FIG. 8. This circuit contains a sense capacitor $C_1$, a reference capacitor $C_2$, and the capacitance, $C_3$, at the gate node of the source follower amplifier (not shown). The voltage at the gate, VG is given by equation (7):

$$V_G=(C_1V_A+C_2V_B)/(C_1+C_2+C_3) \tag{7}$$

The differential response ($\Delta V_G/\Delta C_1$) due to a change in the sense capacitor is given by equation (8):

$$\Delta V_G/\Delta C_1=((C_2+C_3)V_A-C_2V_B)/(C_1+C_2+C_3)^2 \tag{8}$$

If $C_1V_A=-C_2V_B$ so that $V_G=0$ when the pixel is at its nominal temperature, then $\Delta V_G/\Delta C_1 = V_A/C_T$ where $C_T=C_1+C_2+C_3$ is the total capacitance at the node.

The sensor capacitance is given by equation (9):

$$C_1 = \epsilon_0 A/x_e \quad (9)$$

where A is the pixel area and $x_e$ is the equivalent thickness of the capacitor gap, and $x_e = t_r + t_c/\epsilon_c$ where $t_r$ is the thickness of the release layer, and $t_c$ and $\epsilon_c$ are the thickness and relative permittivity of the cap layer (the dielectric overcoat layer 520 in FIG. 5(*a*)), respectively. The change in capacitance induced by a displacement $\Delta x$ is given by equation (10):

$$\Delta C_1 = -\epsilon_0 A \Delta x/x^2 = -C_1 \Delta x/x \quad (10)$$

Therefore, the voltage response to a change in temperature, $R_v = \Delta V_G/\Delta T$, at the detector is given by equation (11):

$$R_v = (\Delta V_G/\Delta C_1)(\Delta C_1/\Delta x)(\Delta x/\Delta Y) \quad (11)$$

The results are shown in Table 3.

TABLE 3

Pixel Performance

| Symbol | Definition | High Performance | Low Cost | Units |
|---|---|---|---|---|
| $L_p$ | L-s absorber length | 49 | 47 | μm |
| $W_p$ | L-4$w_s$-5s absorber width | 37 | 19 | μm |
| $A_p$ | (L-4$w_s$-5s (L-s)) absorber area | 1813 | 893 | μm² |
| $f$ | $A_p/A$ fill factor | 0.725 | 0.357 | |
| $x_c$ | $t_r + t_c/\epsilon_{SiN}$ | 0.54 | 0.567 | μm |
| $C_1$ | $\epsilon_0 A_p/X_c$ sense capacitance | 29.7 | 31.2 | fF |
| $L_h, L_s$ | $L_p$ bi-material and support length | 49 | 47 | μm |
| $\Delta x/\Delta T$ | $K\Delta\alpha L_b^2/t_b$ | 0.174 | 0.08 | μm/K |
| $C_T$ | $3C_1$ total capacitance | 89.1 | 93.6 | fF |
| $R_v$ | $V_A K\Delta\alpha L_b^2/3\chi_e t_b$ | 1.078 | 0.472 | V/K |

Figure 9:
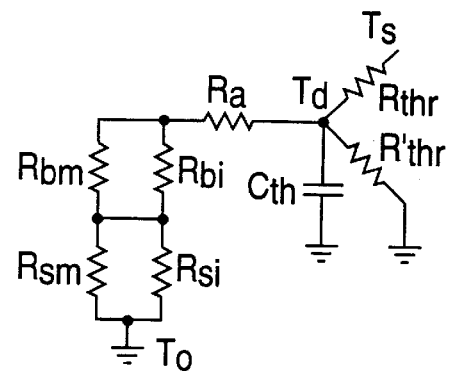
FIG. 9 is a schematic diagram of an exemplary thermal circuit which is useful for describing the thermal behavior of the structure shown in FIG. 2.

The pixel thermal response can be analyzed through the aid of the equivalent circuit shown in FIG. 9. The radiation resistance from the scene to the detector is $R_{thr}$. The radiation resistance between the detector and the substrate is $R'_{thr}$. The lumped thermal capacitance, $C_{th}$, is proportional to the mass, specific heat, and the volume of the absorbing element that consists of the aluminum plate and a layer of silver black that has an area density of 50 μgm/cm² (described in Lang, W,. et al. "Absorbing Layers for Thermal Infrared Radiation", Sensors & Actuators A, 34, (1992) 243–248, and which is hereby incorporated by reference for its teachings on absorbing layers). The total conductive thermal resistance to the silicon substrate is given by equation (12):

$$R_c = R_{bm}\|R_{bi} + R_{sm}\|R_{si} \quad (12)$$

where $R_{bm}$ is in parallel with $R_{bi}$ and $R_{sm}$ is in parallel with $R_{si}$, and $R_a$, $R_{bi}$, $R_{bm}$, $R_{si}$, and $R_{sm}$ are the equivalent lumped thermal resistances of the absorber element (neglected), the insulator and metal layers of the bi-material element, and the insulator and metal layers of the support isolation element, respectively. Note that the metal layer of the support element is the absorber-via metal interconnect. The results are shown in Table 4.

TABLE 4

Pixel Thermal Performance

| Symbol | Definition | High Performance | Low Cost | Units |
|---|---|---|---|---|
| $R_{thr}$ | $1/4\sigma\epsilon_1 L_p W_p B_1 T^3$ | $1.32 \times 10^8$ | $1.83 \times 10^8$ | K/Watt |
| $R'_{thr}$ | $1/4\sigma\epsilon_b L_p W_p B_1 T^3$ | 0 | $1.65 \times 10^9$ | K/Watt |
| $C_{th}$ | $(\rho_{Al}t_s C_{Al} + m_{Ag}C_{Ag}) L_p W_p$ | $1.66 \times 10^{-4}$ | $1.25 \times 10^{-4}$ | joule/K |
| $R_{si}$ | $L_s/2K_{SiN}t_s w_s$ | $1.22 \times 10^7$ | $2.94 \times 10^6$ | K/Watt |
| $R_{sm}$ | $L_s/2K_{Si}t_{va} w_s$ | $4.25 \times 10^7$ | $2.04 \times 10^7$ | K/Watt |
| $R_{bi}$ | $L_b/2K_{Si}t_s w_s$ | $1.22 \times 10^7$ | $2.94 \times 10^6$ | K/Watt |
| $R_{bm}$ | $L_b/2K_{Al}t_s w_s$ | $4.65 \times 10^5$ | $1.15 \times 10^5$ | K/Watt |
| $R_c$ | | $9.96 \times 10^6$ | $2.67 \times 10^6$ | K/Watt |
| $\tau_{th}$ | $(R_c\|R_{thr})C_{th}$ | 16.5 | 3.34 | msec |

In the fabrication of the surface micromachined pixels in an IC facility, the newly developed design rules are applied to generate a mask set that contains two distinct pixel structures. The surface is integrated and pixels are fabricated in an IC facility.

Figure 11:
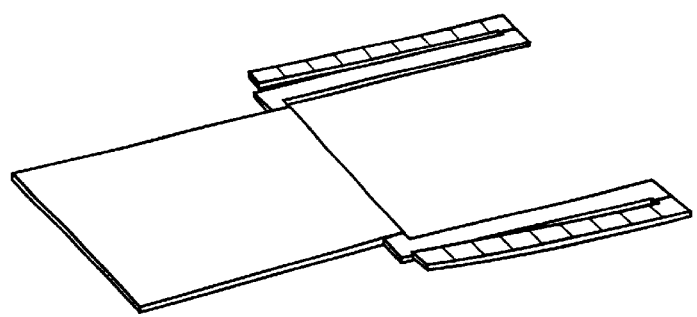
FIG. 11 illustrates a cantilever pixel with folded support in accordance with the present invention.
Figure 12:
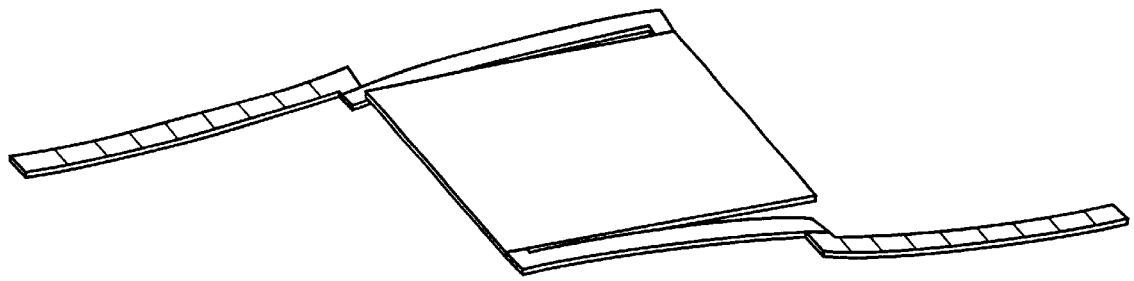
FIG. 12 illustrates a bridge style pixel with extended support in accordance with the present invention.
Figure 15:
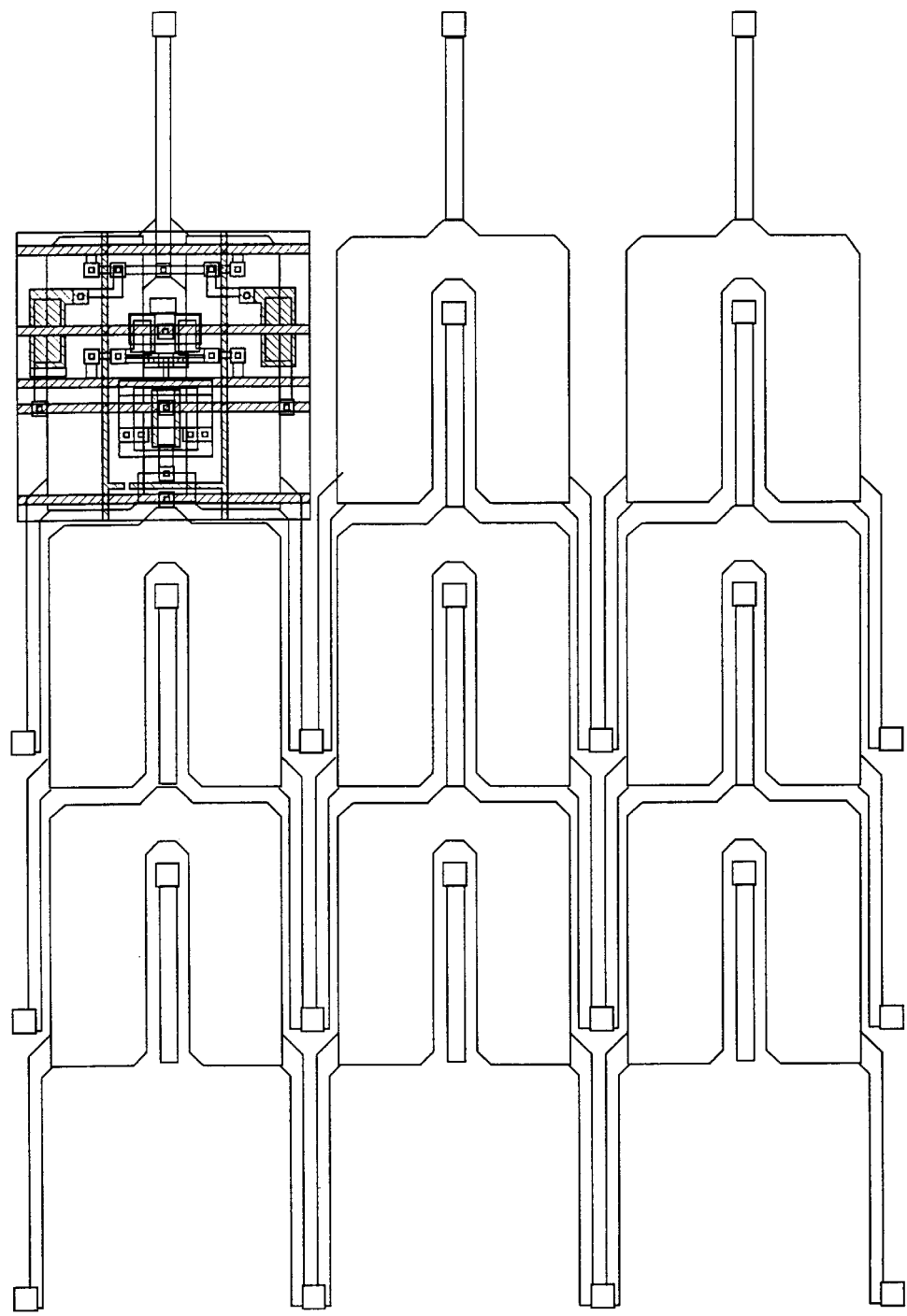
FIG. 15 is a layout design diagram of an array of symmetric bridge style pixels in accordance with the present invention.

More than a dozen possible pixel configurations, three of which are shown in FIGS. 11, 12 and 15, have been postulated. The variation in shading in FIGS. 11 and 12 show the finite element analysis calculated temperature distribution and mechanical movement due to heating at the absorber. Note that the absorber and bi-material elements are nearly at constant temperature. It is not possible to experimentally explore all of these structures at a reasonable time or cost. Therefore, the modeling has been performed on a few most promising structures. For example, the two pixel structures shown in FIGS. 11 and 12 work well. The performance of the cantilever style pixel with folded support of FIG. 11 and bridge style pixel with extended support of FIG. 12 is summarized in Table 5. FIG. 15 shows a symmetric bridge style pixel.

TABLE 5

FEM Modeling Results

| Parameter | Cantilever | Bridge | Units |
|---|---|---|---|
| Spacer | 1 | 1 | μm |
| Support width | 3 | 3 | μm |
| Support thickness | 0.4 | 0.4 | μm |
| Sensitivity | 0.072 | 0.052 | μm/K |
| Thermal resistance | $1.9 \times 10^7$ | $1.7 \times 10^7$ | K/Watt |
| Thermal time constant | 14.9 | 13.5 | msec |
| 1st natural frequency | 18.2 | 27.1 | kHz |
| 2nd natural frequency | 99.6 | 60.8 | kHz |
| Spring constant | 0.038 | 0.087 | N/m |
| Effective dynamic mass | $2.9 \times 10^{-9}$ | $3.0 \times 10^{-9}$ | grams |

Other embodiments of the infrared capacitance sensor are also possible. These include (1) a bridge structure with a bi-material element for increased structural stability, (2) a bridge structure without a bi-material element, relying only on the thermal expansion of the "beam buckling concept" in which the two ends are pinned for increased process simplicity, and (3) variations of the structure where the support arms may be parallel or co-linear with the bi-material element. An example of a bridge structure without a bi-material element is shown in FIG.

Infrared Imaging Array

The room temperature IR imaging array of the present invention involves standard IC processes. The present invention achieves NEΔT in the range of 1 to 10 mK even after accounting for imperfect isolation, limited spectral bandwidth, imperfect absorption, read out transistor noise, and mechanical compromises.

A readout multiplexer for a focal plane imager is made up of an array of the exemplary capacitance sensors. The multiplexer may be fabricated using a standard single-poly double-level-metal CMOS process sequence, on which the capacitance sensor is then formed using planar deposition and etching techniques. Since the sensor is capacitively coupled to the readout multiplexer, no direct electrical connection is required by a capacitive voltage divider circuit which includes a compensation capacitor (with approximately the same value as the sensing capacitor) and in which the sensor and compensator plates are driven with complementary, bi-polar, high-voltage pulsed bias waveforms in order to maximize the signal voltage component and cancel the dc bias components. The capacitive divider is coupled to a low-noise NIOS amplifier (e.g., a source follower) located in each pixel. Horizontal and vertical CMOS scanning registers are used to address and read out the signal from each pixel amplifier.

The manufacturing technology required for the readout multiplexer is a standard CMOS 1-$\mu$m integrated circuit technology. Off-chip electronics have been developed in order to demonstrate the operation of the bi-material detectors as an imaging system. The required manufacturing technology is standard printed circuit board technology.

Since what is being sensed is the relative position of the capacitor plates and since this is not affected by the readout method, the readout noise may be reduced by performing N reads on the same pixel. This technique can reduce noise by a factor of $\sqrt{N}$. Tradeoffs exist, however, between resolution, field size and SNR. For example, a small field of the wide field of view used for tracking targets may be read multiple times to increase the local SNR.

Figure 13:
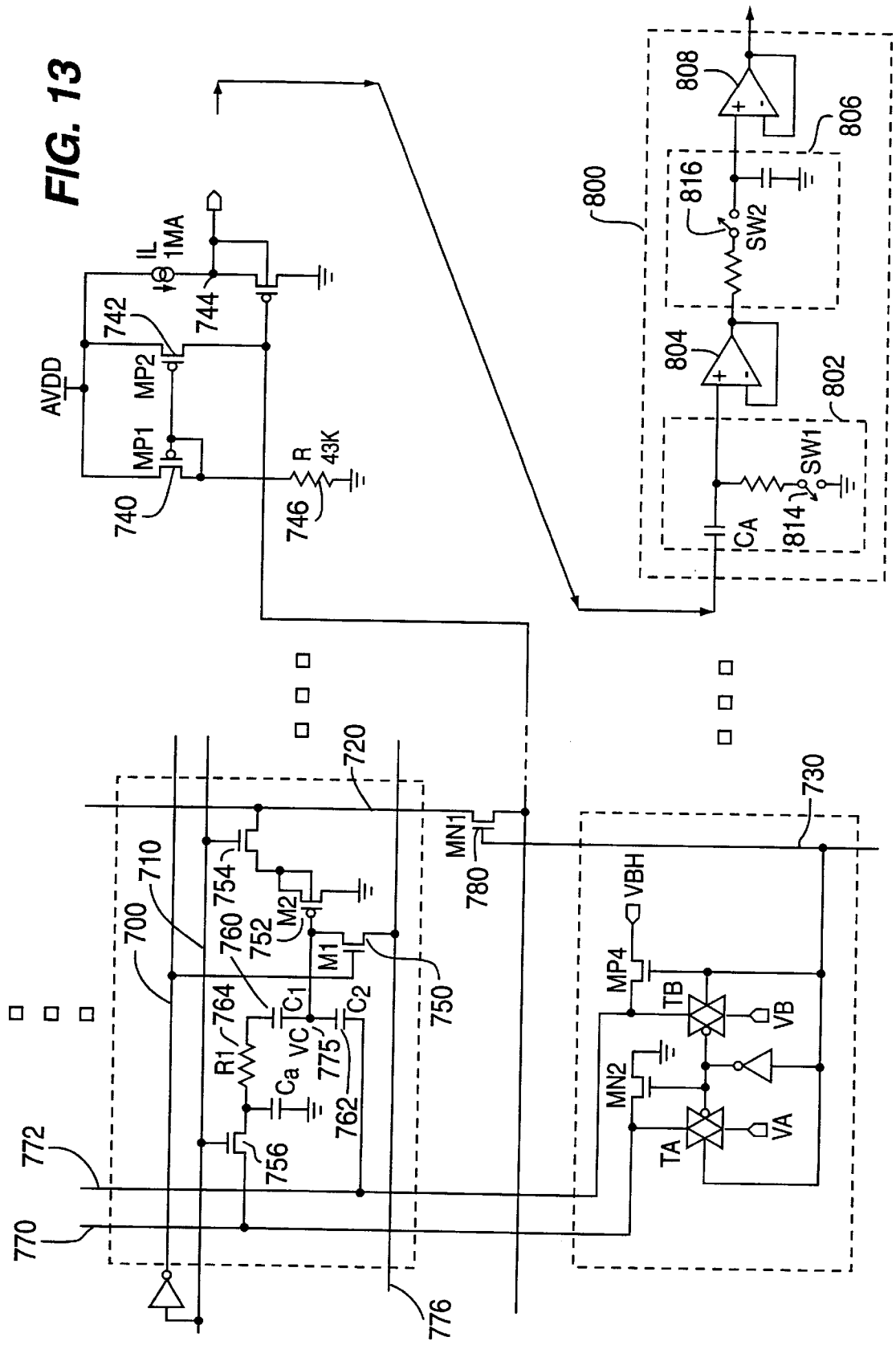
FIG. 13 is a circuit diagram of an exemplary embodiment of a pixel sensor according to the present invention as incorporated into a sensor array.
Figure 14:
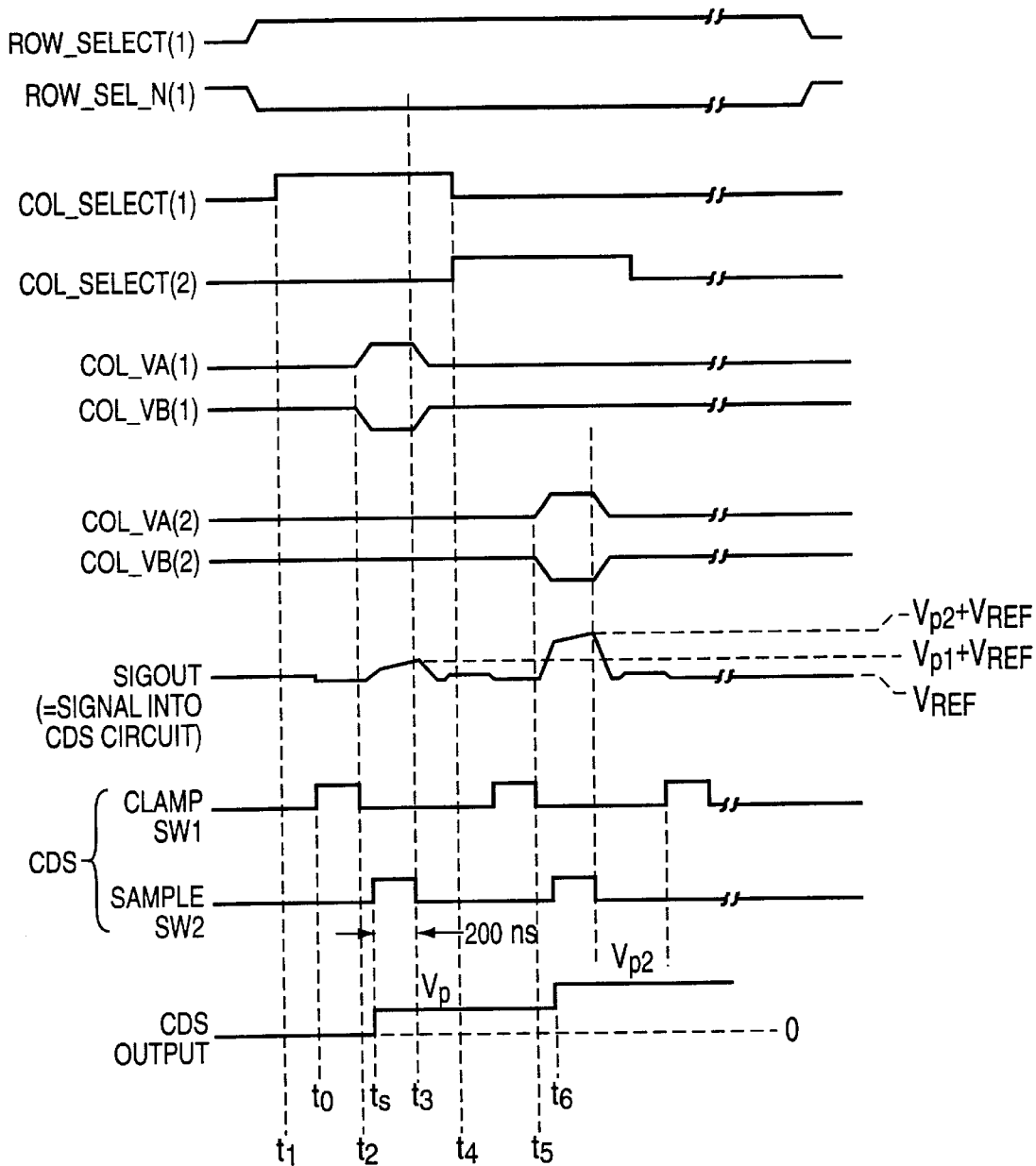
FIG. 14 is a timing diagram of the signal levels applied to the embodiment of FIG. 13.

The read out circuit is a CMOS device that is integrated on a silicon substrate supporting the micromachined IR detector pixels. FIG. 13 shows a schematic diagram of the sensing capacitor Cl and the readout circuit and FIG. 14 shows an illustrative timing diagram. A current mirror consisting of PMOS devices 740 and 742 provides the pixel load current of 0.4 mA for the PMOS source follower 752 located in the selected pixel. This current may be set via an external resistor 746 which has a nominal value of 40 k $\Omega$. In the IR pixel, C1 represents the thermally sensitive variable capacitance 760. Tile top plate of capacitor 760 is connected to the readout circuit by a thin film metal resistor 764. The other components shown in FIG. 13 are integrated in the silicon substrate. A column driver circuit is used to multiplex the common signals $V_A$ and $V_B$ onto one column. This circuit generates the signals COL_VA(X) 770 and COL_VB(X) 772 under the control of the output COL_SELECT(X) 730 which is derived from a conventional horizontal scanning CMOS shift register (not shown). The ROW_SELECT(Y) line 710 is generated by a conventional vertical scanning CMOS shift register (not shown). This signal is inverted to generate the ROW_SEL_N(Y) signal 700 so that the pixels in unselected rows are always in a state with the sense node VG 775 clamped to a reset potential VR 776 which is close to ground. The COL_READ(X) line 720 is a vertical signal line which is multiplexed to a common signal bus via an NMOS transistor 780 and is further buffered by a PMOS source follower 744 to provide an analog signal output SIGOUTT. The output SIGOUT is provided to a CDS circuit 800 which includes a clamp circuit 802, an op-amp voltage follower 804, a sample-and-hold circuit 806, and an op-amp voltage follower 808.

The readout architecture allows the imager array to easily be partitioned into N multiple vertical sections with separate outputs, thereby making it possible to make design tradeoffs between improved readout noise level and more signal outputs. To describe the detailed operation of the readout multiplexer. assume an imager of 320×244 format operating at 30FPS having two 1.25 MHz output ports derived from alternating columns.

In nonselected rows of the imager array, the ROW_SELECT(Y) line 710 is low (e.g., 0 V) and the ROW_SEL_N(Y) line 700 is high (e.g.,+5 V). This turns on the NMOS reset transistor 750 which clamps the common sensing node $V_G$ 775 between capacitors 760 and 762 to the reset potential $V_R$ 776. Transistor 750 is a minimum geometry device (e.g., W=1 $\mu$m and L=1 $\mu$m) which has a source-drain channel resistance of approximately 5 k $\Omega$ under these biased conditions. The ROW_SELECT(Y) line 710 is connected to the gates of the NIOS transistors 754 and 756 and turns both of these devices off. Transistor 754 is used to isolate the COL_READ(X) signal line 720 from the pixel PMOS source follower device 752. Transistor 756 is used to isolate the top plate of capacitor 760 from the COL_VA(X) line 770.

The readout of signals from two pixels (one pixel is shown in FIG. 13) in a selected row is described below with respect to FIG. 14. At the beginning of the readout period, $t_1$, the column select line 730, COL_SELECT(1), of the first pixel, switches to a high level which connects the signal bus and load current source 742 to the column read line 720, COL_READ(1), of the first pixel, as well as to the pixel PMOS source follower 744. Tile row select line 710, ROW_SELECT(1), remains high and the inverted row select line 700, ROW_SEL_N(1), remains low for an entire line time during which all the pixels in a row are read out. The signal output at $t_1$ represents the reference level (SIGOUT=$V_{ref}$) which is used during the clamp period by the external CDS processor 800. The next operation is to pulse the signals $V_A$ and $V_B$ for the first pixel; namely, at time $t_2$, COL_VA(1) switches from low to high and COL_VB(1) switches from high to low. The transitions have relatively slow rise and fall times (about 50 ns) to limit the transient charge displacement current in the reference capacitors 762 located in unselected pixels on the same column. The complementary nature of the $V_A$ and $V_B$ pulses cancels the first order clock transient coupled onto the sensing node while providing a signal component proportional to the variation of the detector capacitor 760 of the form $dV_{out}=dC1*(V_A/CT)$ where CT is the total node capacitance on the sensing node. After a settling time of about 200 ns, the signal is sampled at time $t_3$ (SIGOUT= $V_{ref}+V_{p1}$) by the external CDS circuit 800 and the $V_A$ and $V_B$ pulses return to their respective original levels. The width of the $V_A$ and $V_B$ pulses is minimized in order to limit the mechanical motion induced in the detector capacitor top plate due to electrostatic attractive forces present during the sensing pulse.

After the signal for the first pixel has been sampled and processed by the CDS circuit 800, the signal for the second pixel is read out. At time $t_4$, the column select line 730 of the first pixel, COL_SELECT(1), switches low and the column select line 730 of the second pixel, COL_SELECT(2), switches high. At time $t_5$, the signals $V_A$ and $V_B$ are pulsed for the second pixel; namely, COL_VA(2) switches from low to high and COL_VB(2) switches from high to low. After a settling time of about 200 ns, the signal of the second pixel is sampled at time to (SIGOUT=$V_{ref}+V_{p2}$) by the external CDS circuit 800 and the $V_A$ and $V_B$ pulses return to their respective original levels.

Figure 18:
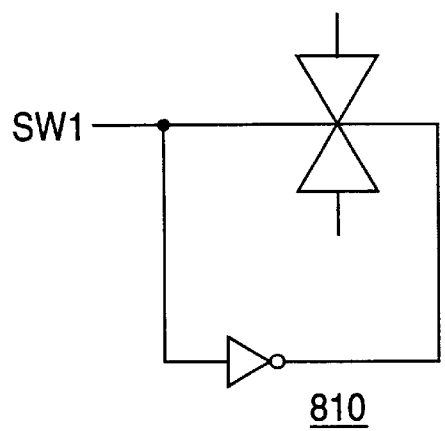
FIG. 18 is a circuit representation of an exemplary transmission gate for use in the embodiment of FIG. 13.

The operation of the CDS circuit 800 with respect to the first pixel in the row is now described. Transmission gates 814 and 816 are represented by switches in FIG. 13. A circuit representation of an exemplary transmission gate 810 for use in the present invention is shown in FIG. 18.

The switching cycles of clocks SW1 and SW2 which control transmission gates 814 and 816, respectively, and the magnitude of the CDS input (SIGOUT) and output signals during the clock cycles are shown in FIG. 14. An input signal of $V_{ref}$ is held by capacitor $C_A$ to establish a clamp level in the clamp circuit 802 when SW1 closes transmission gate 814 at time $t_c$. The stored signal remains at this level after SW1 opens transmission gate 814 at time $t_2$. After SW1 opens transmission gate 814, and SW2 closes transmission gate 816 at time $t_s$, the held input signal, $V_{ref}$, is subtracted from the current input signal, $V_{ref}+V_{p1}$, to give an output signal of $V_{p1}$. This output signal is held in the sample-and-hold circuit 806 and, so, remains $V_{p1}$ after SW2 opens transmission ate 816 at time $t_3$. This signal does not change until SW2 closes transmission gate 816 again. A similar analysis can be performed for the second pixel in the row.

Figure 10:
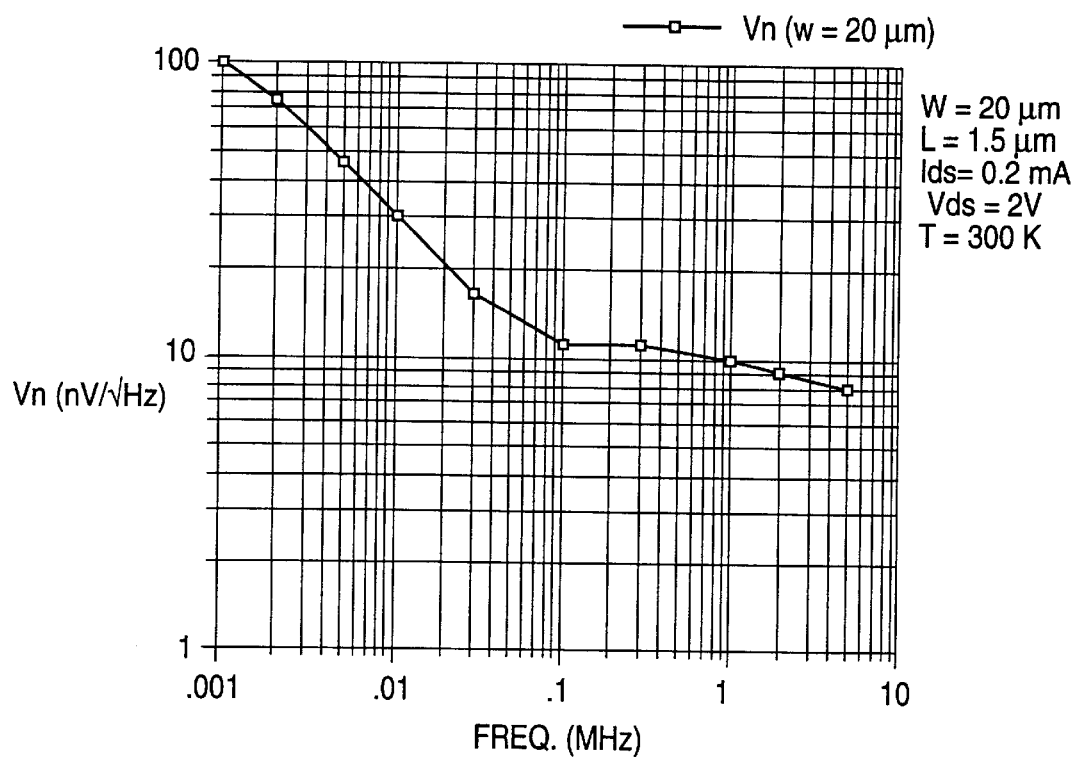
FIG. 10 is a measured amplifier noise diagram which is useful for describing the operation of the circuitry shown in FIG. 4.

A preliminary analysis of the readout noise sources in this design indicates that the predominant noise source is the thermal and trapping noise associated with the pixel source follower transistor 752. The kTC noise generated by resetting the sense node capacitance as well as the 1/f noise in the pixel source follower can be suppressed by correlated double sampling. The thermal noise venerated in the transistor switches 754 and 780 is negligible compared to the pixel source follower because these devices are operating in their linear region as switches with low Vds levels and have a much lower channel resistance. Using a conservative value for the CDS clamp and sample-and-hold time constants of 25 ns, the noise bandwidth of the CDS circuit is about 6.4 MHz. The measured noise level of the PMOS transistor used in the design of a Samoff 640×480 element PtSi imager which is similar in size to the proposed pixel source follower is shown in FIG. 10. At frequencies above the 1/f knee of 0.1 MHz, the equivalent input gate noise for the PMOS transistor is about 10 nV/√Hz. Integrating this value over a noise bandwidth of 6.4 MHz results in a total estimated noise voltage of 25 µV-rms. The results of the NEΔT calculation is given in Table 6.

TABLE 6

Thermal Performance

| Symbol | Definition | High Performance | Low Cost | Units |
|---|---|---|---|---|
| $\epsilon_b$ | Bottom emissivity | 0 | 0.1 | |
| $\epsilon_t$ | Top emissivity | 1 | 0.9 | |
| λ | Upper wavelength | 30 | 14 | µm |
| $B_\lambda$ | Spectral bandwidth factor | 1.323 | 2.649 | |
| $1 + \epsilon_b/\epsilon_t$ | Bottom radiation effect | 1 | 1.11 | |
| $1 + R_{thr}/R_c$ | Thermal shunting due to support element | 13.2 | 68.5 | |
| β | Thermal transfer function | 70.1 | 806 | |
| $\Delta T_{rms}$ | Photon shot noise | 31.6 | 27.3 | µK |
| NEΔT | Thermal | 1.91 | 22 | mK |
| NEΔT | Amplifier | 1.75 | 20.1 | mK |
| NEΔT | Total | 2.59 | 29.8 | mK |

Shot noise is common to all IR imagers and limits the ultimate capability of an uncooled IR imager. Table 7 shows the specification of an ideal imager which has perfect thermal isolation from the supporting substrate. Table 8 shows the ultimate performance based on photon shot noise.

TABLE 7

Ideal Imager Specifications

| Quantity | Value | Units |
|---|---|---|
| Frame rate | 30 | 1/sec |
| Thermal time constant, $\tau_{th}$ | 10 | msec |
| Absorber top side emissivity, $\epsilon$ | 1 | |
| Absorber bottom side emissivity | 0 | |
| IR spectral band | 1 to 100 | µm |
| Fill factor, f | 100 | % |
| Pixel area, A | 2500 | µm² |
| F number, F | 1 | |

TABLE 8

Ultimate Performance Limit

| Quantity | Formula | Value | Units |
|---|---|---|---|
| Radiation thermal resistance | $R_{thr} = 1/4\epsilon\sigma fAT^3$ | $6.53 \times 10^7$ | W/K |
| Thermal Capacitance | $C_{th} = \tau_{th}/R_{thr}$ | $1.53 \times 10^{-10}$ | J/K |
| Photon shot noise | $\sqrt{\Delta T_n^2} = T_d \sqrt{k} / C_{th}$ | $9.09 \times 10^{-5}$ | K |
| Optical-thermal transfer coefficient | $\beta = dT_s/dT_d = 4F^2 B_\lambda$ | 4 | |
| NEΔT | $NE\Delta T_{thermal} = \beta\sqrt{\Delta T_n^2}$ | 0.36 | mK |

$T_s$ is the scene temperature, $T_d$ is the detector temperature and $B_{80}$ is the inverse of the fractional portion of the spectral excitance of the scene received by the absorber. All approaches to an uncooled IR imager are limited by the factors shown. However, uncooled IR imagers differ in the level of thermal isolation, emissivity of the absorber, $B_{80}$ and sensitivity of the thermal sensing mechanism. The first two mechanisms affect the optical thermal transfer coefficient, given by equation (13):

$$\beta = 4F^2 B_\lambda (1 + R_{thr}/R_{th})(1 + \epsilon_b/\epsilon_t) \quad (13)$$

which prefixes all of the contributors to NEΔT including that of the sensor, given by equation (14):

$$NE\Delta T_{sensor} = \beta\sqrt{\Delta v_n^2}\left(\frac{dV}{dT}\right)^{-1} \quad (14)$$

There are two ways improve imager NEΔT: 1) reduce β by increasing isolation and IR absorption, and 2) increase sensitivity, dV/dT. Methods to reduce β are common to all imager approaches, but the singular advantage of the current approach over other approaches utilizing thermistors or ferroelectrics is the sensitivity of the detection mechanism. Here, an order of magnitude improvement is shown without having to discover new materials.

A unique feature of the IR detector readout multiplexer is that gain and offset variations in the signal read from each pixel may be compensated directly on the imager by modulating the amplitude of the $V_A$ and $V_B$ pulses applied to the pixels. The modulation may be implemented by driving the high level of $V_A$ and the low level of $V_B$ with the output of two D/A converters. The digital input data for the D/A converters is obtained from REM or ROM stored offset values for each pixel. Therefore, the local nonuniformity in offset can be canceled. Similarly, since the detector response is proportional to $V_A$, the overall gain can also be adjusted. These corrections are desirable because they allow the device to retain a good dynamic range while achieving high sensitivity.

The signal voltage, $V_{out}$, produced at the gate of the pixel source follower may be calculated from the superposition components due to $V_A$ and $V_B$, as shown in equation (15):

$$V_{out}=(C1V_A+C2V_B)/CT \qquad (15)$$

where CT is the total capacitance on $V_{out}$.

As an example of a gain offset correction, if the D/A converter modulation on the $V_A$ and $V_B$ amplitude is chosen such that $dV_B=-dV_A(C1/C2)$, then a gain change of $dV_A/V_A$ will result without introducing any change in the offset voltage.

Figure 16:
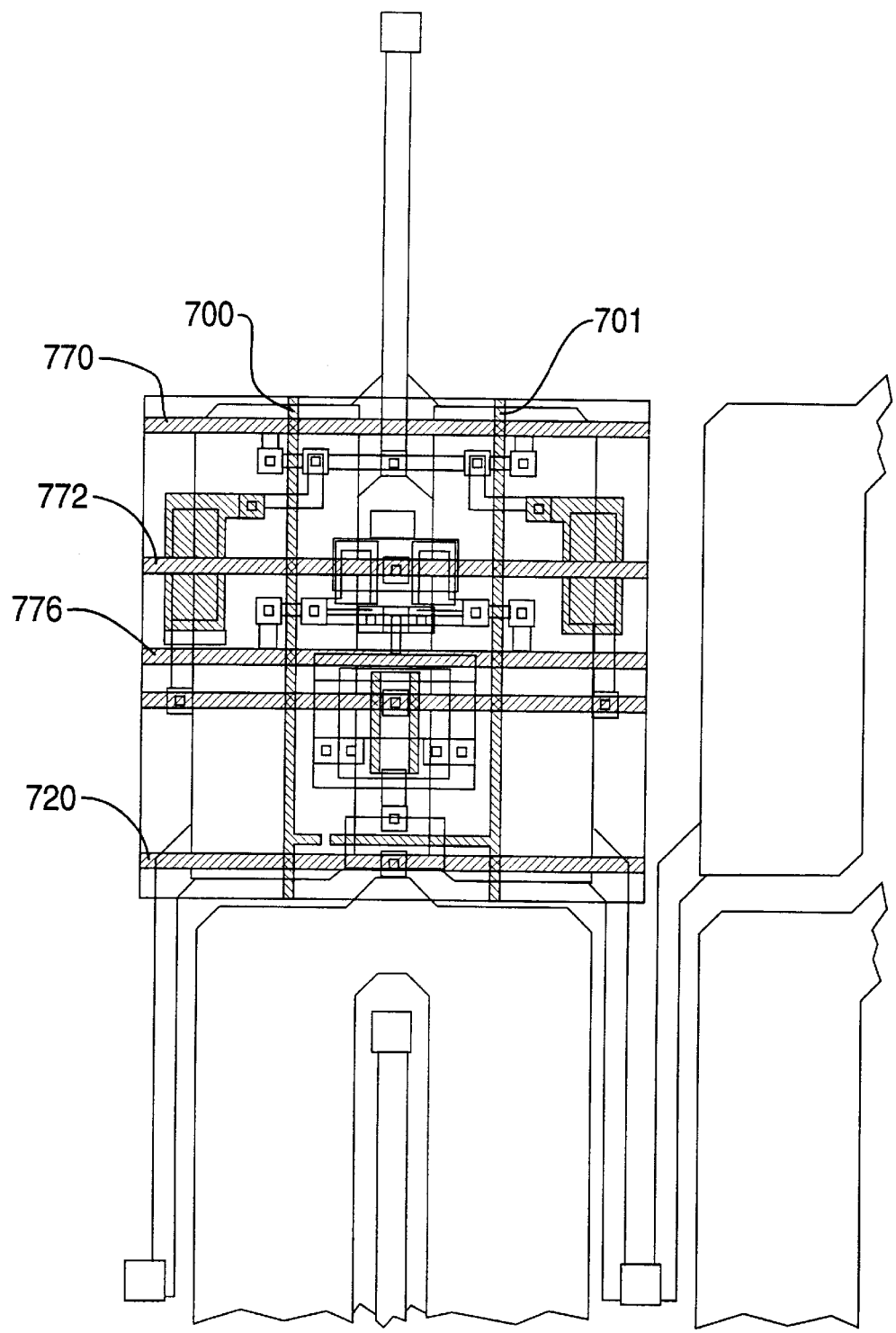
FIG. 16 is an enlarged view of one of the pixels of the exemplary embodiment of FIG. 15.
Figure 17:
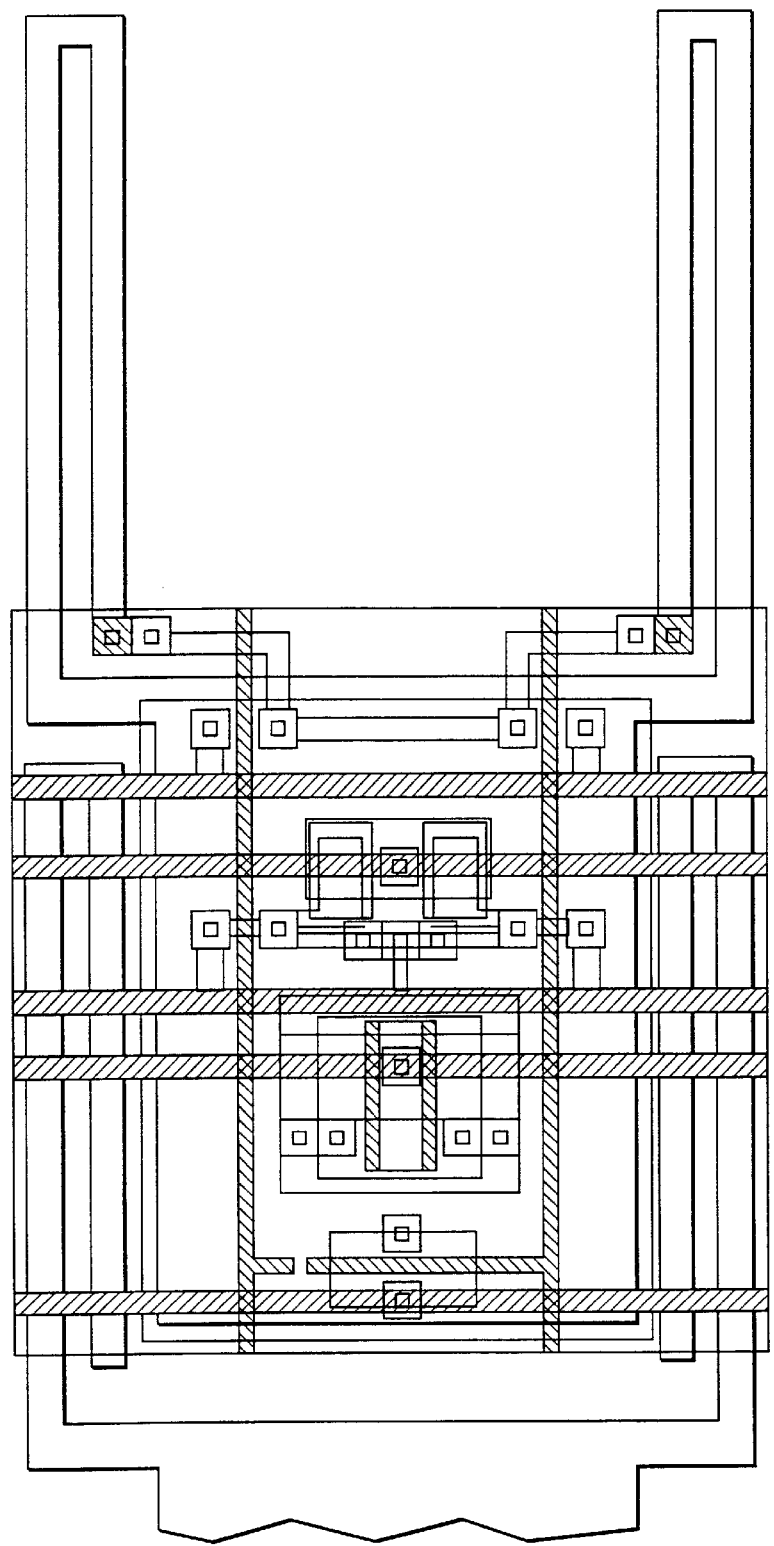
FIG. 17 is a layout design diagram of a cantilevered style pixel in accordance with the present invention.

FIGS. 15 and 16 show a CMOS design layout at different zoom levels for an exemplary CMOS readout circuit for an array of symmetric bridge style pixels. FIG. 17 shows a CMOS design layout for a cantilevered style pixel which can be incorporated into an array of pixels similar to that shown in FIG. 15.

The key to calculating NEAT is the determination of the change of detector temperature with respect to a change in scene temperature (described in Jensen, A. S., "Limitations to Room Temperature IR Imaging Systems", SPIE Vol. 2020 Infrared Technology MX (1993), and which is hereby incorporated by reference for its teachings on NEΔT). Defining the thermal transfer coefficient as $\beta=dT_s/dT_d$ where $T_s$ and $T_d$ are the scene and detector temperatures, respectively, NEΔT for any system can be computed from the quadrature addition of individual contributions, as shown in equation (16):

$$NE\Delta T_k=\beta N_{rms}/S_k \qquad (16)$$

where $N_{rms}$ is the rms value of the noise source associated with $S_K$, the signal sensitivity per K at the detector. For example, the component due to amplification electronics is given by equation (17):

$$NE\Delta T_{amp} = \beta\sqrt{\overline{v_a^2}}/R_v \qquad (17)$$

where $$\sqrt{\overline{v_a^2}}$$

is the rms value of the equivalent input noise voltage to the source follower amplifier. Similarly, equation (18) gives the thermal component of $$NE\Delta T_{THERMAL} = \beta\sqrt{\overline{\Delta T_n^2}} \qquad (18)$$

where $$\sqrt{\overline{\Delta T_n^2}}$$

is the thermal fluctuation of photon shot noise; in this case, the signal sensitivity coefficient is composed of several factors such as the imaging optics, the spectral bandwidth, and the thermal shunting due to parasitic thermal resistance to the ambient. Thus, as stated above, the thermal transfer coefficient is given by equation (13):

$$\beta=4F^2B_\lambda(1+R_{thr}/R_c)(1+\epsilon_b/\epsilon_t) \qquad (13)$$

where $4F^2$ is due to the imaging optics. If the absorption in the path between the source and the absorber and the spectral efficiency of the absorber are modeled as a rectangular spectral band pass function, then the spectral bandwidth factor is given by equation (19):

$$B_\lambda=\sigma T^4/\int_8^\lambda M_e(\lambda,T)d\lambda \qquad (19)$$

where the lower wavelength limit is set at 8 $\mu$m due to atmospheric absorption. The upper wavelength limit will be set by the absorber spectral properties and IR lens used by the imager. BA is assumed to be relatively independent of temperature. The photon shot noise can be shown to be given by equation (20):

$$\Delta T_{rms}=\sqrt{k/C_{th}}T \qquad (20)$$

(described in Hanson, C., "Uncooled Thermal Imaging at Texas Instruments", SPIE Vol. 2020 Infrared Technology XIX (1993), and which is hereby incorporated by reference for its teachings on shot noise).

When the capacitance is sensed by the voltage pulse of magnitude $V_A$, the absorber plate is attracted to the matching electrically conductive (e.g., metal) plate buried in the substrate with a force equal to $F=C_1V_A^2/x$ and begins to move towards the substrate surface. This behavior can be modeled using a lumped element model as given by equation (21):

$$md^2x/dt^2=\epsilon AV_A^2/x^2-k(i_o-x) \qquad (21)$$

where m and k are the lumped element equivalent mass and spring constant of the mechanical system. When the pulse is removed 0.1 $\mu$sec later, a significant amount of energy has been imparted to the plate consisting of mechanical energy due to the motion of the plate and potential energy due to the elastic bending of the support. In the absence of any damping action, this results in the detector plate vibrating freely until the next sense pulse. An extreme estimate of this effect can be made by ignoring the nonlinearities and the spring constant. The approximate displacement and energy imparted during the sense pulse application are given by equations (22) and (23), respectively:

$$d=(C_1V_A^2/2mx)t_p^2 \qquad (22)$$

$$E=(C_1V_A^2/x)^2t_p^2/2m \qquad (23)$$

Since there is no natural mechanism to quench these vibrations, the mechanical system is coupled back into the electronic system during the reset period. In this case, the electromechanical system will follow equation (24):

$$\frac{d}{dt}\left(\frac{1}{2}m\left(\frac{dx}{dt}\right)^2+\frac{1}{2}k(x-x_o)^2+\frac{1}{2}C(V_R-I_CR)^2\right)=-RI_C^2 \qquad (24)$$

$$I_C=d(C(V_R-RI_C))/dt \qquad (25)$$

An estimate of the behavior described is shown in Table 9. The residual resistance of the reset transistor and the series resistance in the support element combine to dissipate the stored energy.

TABLE 9

Mechanical Behavior

| Symbol | Definition | High Performance | Low Cost | Units |
|---|---|---|---|---|
| m | $(\rho_{Al}t_s + m_{Ag})A_p$ | $1.89 \times 10^{-9}$ | $1.41 \times 10^{-9}$ | gm |
| $t_p$ | sense pulse width | 0.1 | 0.2 | $\mu$sec |
| d | detector plate displacement | 0.015 | 0.061 | $\mu$m |
| E | energy imparted | $8.0 \times 10^{-14}$ | $2.64 \times 10^{-13}$ | joule |
| $V_R$ | reset voltage | 0.1 | 0.1 | Volt |
| R | reset circuit resistance | 1000 | 1000 | $\Omega$ |
| $V_R^2/R$ | initial power dissipation | $10^{-5}$ | $10^{-5}$ | Watt |

Higher aspect ratios and further improvement in NE$\Delta$T can be achieved if the usual 4:3 display characteristic is ignored. For example, a 2:1 aspect ratio pixel with the 2500 $\mu$m$^2$ area has sides 70.7 $\mu$m and 35.3 $\mu$m and will yield a reduction in NE$\Delta$T by a factor of 2.83.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A method of detecting radiation, comprising the steps of:
    providing a microcantilever within a substrate, including the steps of: providing a base for coupling said microcantilever to said substrate and providing a thermal isolation element for isolating said microcantilever from said substrate wherein the microcantilever has at least one physical property that is affected by radiation;
    exposing said microcantilever to a source of radiation;
    monitoring a radiation-induced change in the at least one physical property of the microcantilever to determine a magnitude of the change; and
    determining a measure of the radiation from the magnitude of the radiation-induced changes in the at least one physical property of the microcantilever.

2. The method according to claim 1, wherein the monitoring step includes monitoring radiation-induced bending of the microcantilever.

3. The method as in claim 1, wherein said microcantilever includes a film made of a material which interacts with the microcantilever to form a bi-material element.

4. The method as in claim 3, wherein said bi-material element heats when exposed to radiation and said change in the at least one physical property comprises bending.

5. A sensor for detecting radiation in response to a radiation-induced change, comprising:
    a microcantilever formed within a substrate and including at least one physical property that is affected by radiation, a base coupling said microcantilever to said substrate, and a thermal isolation element isolating said microcantilever from said substrate; and
    means for determining a measure of a radiation-induced change in the at least one physical property;
    wherein said radiation-induced change comprises a change in the at least one physical property of the microcantilever.

6. The sensor as in claim 5, wherein said microcantilever further includes a film made of a material which interacts with the microcantilever to form a bi-material element.

7. The sensor as in claim 6, wherein said bi-material element heats when exposed to radiation and said change in the at least one physical property comprises bending.

* * * * *

UNITED STATES PATENT AND TRADEMARK OFFICE
CERTIFICATE OF CORRECTION

PATENT NO. : 6,249,001 B1  Page 1 of 1
APPLICATION NO. : 09/300986
DATED : June 19, 2001
INVENTOR(S) : Donald Jon Sauer et al.

It is certified that error appears in the above-identified patent and that said Letters Patent is hereby corrected as shown below:

Title Page, item (22)
On the cover sheet the filing date reads "Apr. 8, 1999" but should read --Apr. 28, 1999--.

Signed and Sealed this

Nineteenth Day of February, 2008

JON W. DUDAS
*Director of the United States Patent and Trademark Office*